(12) United States Patent
Watts

(10) Patent No.: US 6,228,396 B1
(45) Date of Patent: May 8, 2001

(54) COLONIC DRUG DELIVERY COMPOSITION

(75) Inventor: Peter Watts, Nottingham (GB)

(73) Assignee: West Pharmaceutical Services Drug Delivery & Clinical Research Centre Limited, Nottingham (GB)

( * ) Notice: Subject to any disclaimer, the term of this patent is extended or adjusted under 35 U.S.C. 154(b) by 0 days.

(21) Appl. No.: 08/765,347

(22) PCT Filed: Jun. 21, 1995

(86) PCT No.: PCT/GB95/01458

§ 371 Date: Feb. 10, 1997

§ 102(e) Date: Feb. 10, 1997

(87) PCT Pub. No.: WO95/35100

PCT Pub. Date: Dec. 28, 1995

(30) Foreign Application Priority Data

Jun. 21, 1994 (GB) .................................................. 9412394

(51) Int. Cl.⁷ ...................................................... A61K 9/48
(52) U.S. Cl. ......................... 424/463; 424/452; 424/456; 424/459
(58) Field of Search .................... 424/463, 451, 424/452, 459

(56) References Cited

U.S. PATENT DOCUMENTS

| | | |
|---|---|---|
| 4,663,308 | 5/1987 | Saffran et al. . |
| 4,673,438 * | 6/1987 | Wittwer .................. 106/126 |
| 4,738,724 * | 4/1988 | Wittwer .................. 106/213 |
| 4,945,080 * | 7/1990 | Lindstrom ................ 514/29 |
| 5,342,624 * | 8/1994 | McNeill .................. 424/451 |
| 5,444,041 * | 8/1995 | Owen ..................... 514/2 |
| 5,514,663 | 5/1996 | Mandel . |
| 5,622,721 * | 4/1997 | Dansereau ............... 424/490 |
| 5,631,022 | 5/1997 | Mandel et al. . |
| 5,651,983 * | 7/1997 | Kelm ..................... 424/452 |
| 5,656,290 | 8/1997 | Kelm et al. . |
| 5,670,158 | 9/1997 | Davis et al. . |
| 5,686,105 | 11/1997 | Kelm et al. . |
| 5,686,106 | 11/1997 | Kelm et al. . |
| 5,707,648 * | 1/1998 | Yiv ...................... 424/450 |

FOREIGN PATENT DOCUMENTS

| | | |
|---|---|---|
| 42 36 025 | 4/1994 | (DE) . |
| 0 225 189 * | 10/1987 | (EP) . |
| 0 338 383 | 10/1989 | (EP) . |
| 0 621 032 | 10/1994 | (EP) . |
| 0 673 645 | 9/1995 | (EP) . |
| 2 166 051 | 4/1986 | (GB) . |
| 2 174 599 | 11/1986 | (GB) . |
| 89/11269 | 11/1989 | (WO) . |
| 90/13286 | 11/1990 | (WO) . |
| 91/11175 * | 8/1991 | (WO) . |
| 95/06464 | 3/1995 | (WO) . |

OTHER PUBLICATIONS

Burns, et al., "An in vitro assessment of liquid–filled Capill® potato starch capsules with biphasic release characteristics," *Int'l J. Pharmaceutics,* 134: 223–30 (1996).

Kenyon, et al., "The effect of food on the vivo behaviour of enteric coated starch capsules," *Int'l J. Pharmaceutics,* 112: 207–13 (1994).

* cited by examiner

*Primary Examiner*—Fred Zitomer
(74) *Attorney, Agent, or Firm*—Arnall Golden & Gregory, LLP

(57) ABSTRACT

A colonic drug delivery composition is provided and comprises a starch capsule containing a drug, the starch capsule being provided with a coating such that the drug will only be released from the capsule in the colon. The coating may be a pH sensitive material, a redox sensitive material, or a material broken down by specific enzymes or bacteria present in the colon. The drug to be delivered may be one for local action in the colon or a systemically active drug to be absorbed from the colon.

13 Claims, 2 Drawing Sheets

COLONIC DRUG DELIVERY COMPOSITION

The present invention relates to a drug delivery composition for delivering a drug to the colon.

There is currently considerable interest in the development of pharmaceutical formulations which are capable of selective delivery of drugs into the colon. Site specific delivery to the colon can have two major advantages for the development of pharmaceutical products:

1. Treatment of local conditions: colonic diseases which may benefit from selective delivery of drug include Crohns disease and ulcerative colitis, where established therapies include corticosteroids and mesalazine (5-aminosalicylic acid), irritable bowel syndrome (antimotility drugs, antiinflammatories), spastic colon (anticholinergics), constipation (laxatives) and colon cancer (antineoplastics).
2. Improved absorption of difficult drugs: the products of biotechnology, such as peptides and proteins and carbohydrate drugs, are difficult to deliver except by injection. The ability to delivery such compounds orally can be of great importance. The colon is often identified as a preferred site because of slow transit, low volume and a lack of vigorous stirring, leading to an ability to create local conditions favourable to stabilisation and absorption enhancement, and a lack of digestive enzymes (proteases).

There are a number of technologies, both marketed and in development, that are claimed to provide colon specific delivery of drugs.

Two devices in which drug release is claimed to be entirely time-dependent dependent include the Pulsincap™ (WO 90/09168) and the Time Clock Release System™ (Pozzi et al., APV course on Pulsatile Drug Delivery, Königswinter, May 20, 1992).

Site-specific delivery into the colon can also be achieved by the use of coating material that are specifically degraded in the colonic environment by the action of microorganisms and/or the reductive environment found there. Such materials include but are not limited to azopolymers and disulphide polymers (PCT BE91/00006), amylose (Milojevic et al, Proc. Int. Symp. Contr. Rel. Bioact. Mater., 20, 288, 1993), calcium pectinate (Rubenstein et al., Pharm. Res., 10, 258–263, 1993) chondroitin sulphate (Rubenstein et al., Pharm. Res., 9, 276–278, 1992), and modified guar gum (Rubenstein and Gliko-Kabir, S. T. P. Pharma Sciences 5, 41–46, 1995).

Site-specific delivery into the small intestine has been achieved for many years by the use of pH-sensitive (enteric) coatings. By applying more coating and/or raising the threshold pH at which dissolution of the coating begins, it is possible to achieve colon-specific delivery by the use of enteric polymers. Tablets containing mesalazine and coated with Eudragit S100, which dissolves above pH 7, are marketed in a number of countries (Asacol™, SmithKline Beecham in UK). Although this formulation is generally successful in achieving site-specific delivery of 5-ASA, failure of the coating to dissolve has been reported, with patients observing intact tablets in their stools (Schroeder et al., New Engl. J. Med., 317, 1625–1629, 1987). Mesalazine tablets coated with Eudragit L100, which dissolves above pH 6, are also commercially available (e.g. Claversal™ and Salofalk™). A scintigraphic assessment indicated that in a group of thirteen patients more than 70% of administered Claversal tablets disintegrated in the lower small intestine, on average 3.2 h after gastric emptying (Hardy et al., Aliment. Pharmacol. Therap., 1, 273–380, 1987). Although enteric coatings are one of the simplest technologies available for colon-specific delivery, they also offer an advantage in terms of cost and ease of manufacture.

Coated dosage forms for colonic delivery are almost exclusively based on tablets. However, there are circumstances in which it would be beneficial to use a coated capsule formulation e.g. where the material to be delivered is a liquid, or is sensitive to compression. The known capsules are typically made from gelatin. Although it is possible to coat hard gelatin capsules, there are a considerable number of drawbacks with such a product. In particular, the capsule shell becomes brittle during coating or on long term storage. Furthermore, the smooth surface of the gelatin shell results in poor adhesion of the coating, there is a risk of the coat cracking on handling the capsule, and there is an interaction of the coating with the gelatin shell resulting in changed dissolution performance on long term storage. For these reasons an enteric capsule has not been an obvious choice if an enteric drug delivery device has to be selected.

Surprisingly we have now discovered that the drawbacks of the gelatin capsules and the general prejudice of capsules being unsuitable for enteric coating for colon delivery can be minimised by the use of injection moulded starch capsules.

The invention therefore provides a drug delivery composition for delivering a drug to the colonic region comprising a starch capsule containing the drug and wherein the starch capsule is provided with a coating such that the drug is predominantly released from the capsule in the colon and/or terminal ileum.

Preferably, substantially all of the drug is released in the terminal ileum and/or the colon.

The term "starch" is used to include modified starches and starch derivatives. The starches used should be of food or pharmaceutical quality.

By the term "derivatives" we particularly mean ester and ethers of the parent compound that can be unfunctionalised or functionalised to contain, for example, ionic groupings.

Suitable starch derivatives include hydroxyethyl starch, hydroxypropyl starch, carboxymethyl starch, cationic starch, acetylated starch, phosphorylated starch, succinate derivatives or starch and grafted starches. Such starch derivatives are well known and described in the art (for example Modified Starches: Properties and Uses, O. B. Wurzburg, CRC Press Boca Raton (1986)).

The starch capsules are sold oral dosage forms in which a drug is enclosed in a starch container, which disintegrates in contact with water. The capsules may also contain dyes, opaquing agents such as titanium dioxide, dispersing agents and mould releasing agents. The capsules typically also contain between 12% and 16% of water.

The capsules are made using an injection moulding process. They comprise two components, a body and a cap. The body is filled with the drug to be delivered and the cap is then attached and sealed. Unlike gelatin capsules, there is no overlap between the body and the cap of the starch capsule and this allows for easy application of the coating. The method of making the starch capsules is well known in the art, and capsules and their method of manufacture described in EP-A-118240, WO-90/05161, EP-A-0304401, WO-92/04408 or GB-2187703 can be used.

The composition of the coating should be optimised to maximise disintegration of the coating within the colon whilst minimising the possibility of the coated capsules passing through the gastrointestinal tract intact.

Any coating can be used which ensures that the capsule does not break-up and release the drug until it is in the colon. The coating may be one which is pH-sensitive, redox-sensitive or sensitive to particular enzymes or bacteria, such that the coating only dissolves or finishes dissolving in the colon. Thus the capsules will not release the drug until it is in the colon.

The thickness of the coating will typically be in the range of 80 μm to 300 μm. The thickness of the particular coating used will be chosen according to the mechanism by which the coating is dissolved.

Preferred coating materials are those which dissolve at a pH of 5 or above. The coatings therefore only begin to dissolve when they have left the stomach and entered the small intestine. A thick layer of coating is provided which will dissolve in about 3–4 hours thereby allowing the capsule underneath to breakup only when it has reached the terminal ileum or the colon. Such a coating can be made from a variety of polymers such as cellulose acetate trimellitate (CAT), hydroxypropylmethyl cellulose phthalate (HPMCP), polyvinyl acetate phthalate (PVAP), cellulose acetate phthalate (CAP) and shellac as described by Healy in his article "Enteric Coatings and Delayed Release" Chapter 7 in Drug Delivery to the Gastrointestinal Tract, editors Hardy et al., Ellis Horwood, Chichester, 1989. For coatings of cellulose esters, a thickness of 200–250 μm would be suitable.

Especially preferred materials are methylmethacrylates or copolymers of methacrylic acid and methylmethacrylate. Such materials are available as Eudragit polymers (trademark) (Rohm Pharma, Darmstadt, Germany). Eudragits are copolymers of methacrylic acid and methylmethacrylate. Preferred compositions are based on Eudragit L100 and Eudragit S100. Eudragit L100 dissolves at pH 6 and upwards and comprises 48.3% methacrylic acid units per g dry substance; Eudragit S100 dissolves at pH 7 and upwards and comprises 29.2% methacrylic acid units per g dry substance. Preferred coating compositions are based on Eudragit L100 and Eudragit S100 in the range of 100 parts L100:0 parts S100 to 20 parts L100:80 parts S100. The most preferable range is 70 parts L100:30 parts S100 to 80 parts L100:20 parts S100. As the pH at which the coating begins to dissolve increases, the thickness necessary to achieve colon specific delivery decreases. For formulations where the ratio of Eudragit L100:S100 is high, a coat thickness of the order 150–200 μm is preferable. This is equivalent to 70–110 mg of coating for a size 0 capsule. For coatings where the ratio Eudragit L100:S100 is low, a coat thickness of the order 80–120 μm is preferable, equivalent to 30 to 60 mg coating for a size 0 capsule.

The colonic region has a high presence of microbial anaerobic organisms providing reducing conditions. Thus the coating may suitably comprise a material which is redox-sensitive. Such coatings may comprise azopolymers which can for example consist of a random copolymer of styrene and hydroxyethyl methacrylate, cross-linked with divinylazobenzene synthesized by free radical polymerization, the azopolymer being broken down enzymatically and specifically in the colon, or disulphide polymers (see PCT/BE91/00006 and Van den Mooter, Int. J. Pharm. 87, 37, 1992).

Other materials which providing release in the colon are amylose, for example a coating composition can be prepared by mixing amylose-butan-1-ol complex (glassy amylose) with Ethocel aqueous dispersion (Milojevic et al., Proc. Int. Symp. Contr. Rel. Bioact. Mater. 20, 288, 1993), or a coating formulation comprising an inner coating of glassy amylose and an outer coating of cellulose or acrylic polymer material (Allwood et al GB 9025373.3), calcium pectinate (Rubenstein et al., Pharm. Res., 10, 258, 1993) pectin, a polysaccharide which is totally degraded by colonic bacterial enzymes (Ashford et al., Br Pharm. Conference, 1992, Abstract 13), chondroitin sulphate (Rubenstein et al. Pharm. Res. 9, 276, 1992) and resistant starches (Allwood et al., PCT WO 89/11269, 1989), dextran hydrogels (Hovgaard and Brøndsted, 3rd Eur. Symp. Control. Drug Del., Abstract Book, 1994, 87) modified guar gum such as borax modified guar gum (Rubenstein and Gliko-Kabir, S. T. P. Pharma Sciences 5, 41–46, 1995), β-cyclodextrin (Sid ke et at., Eu. J. Pharm. Biopharm. 40 (suppl), 335, 1994), saccharide containing polymers, by which we include a polymeric construct comprising a synthetic oligosaccharide-containing biopolymer including methacrylic polymers covalently coupled to oligosaccharides such as cellobiose, lactulose, raffinose and stachyose, or saccharide-containing, natural polymers including modified mucopolysaccharides such as cross-linked pectate (Sintov and Rubenstein PCT/US 91/03014); methacrylate-galactomannan (Lehmann and Dreher, Proc. Int. Symp. Control. Rel. Bioact. Mater. 18, 331, 1991) and pH-sensitive hydrogels (Kopecek et al., J. Control. Rel. 19, 121, 1992). Resistant starches, eg glassy amylose, are starches that are not broken down by the enzymes in the upper gastrointestinal tract but are degraded by enzymes in the colon.

The drug which is contained in the capsule may be any pharmaceutically or therapeutically active agent. The term "drug" is used herein to include any active agent that can have its effect locally or in the body after systemic absorption into the circulation or transport via the lymphatic system. The term also includes antigens and allergens for use as vaccine as well as DNA for use in gene therapy.

The starch capsules are especially advantageous over gelatin capsules because they can be filled with drug in any form including liquids, powders, pellets and mini-tablets.

The drug may be one which is locally acting in the colonic region to treat a colon disease such as irritable bowel syndrome, irritable bowel disease, crohns disease, constipation, post operative atony, gastrointestinal infections and for delivery of an antigenic material to the lymphoid tissue. Such drugs include those for the treatment of colon disease, for example, 5-ASA; steroids such as hydrocortisone, budesonide; laxatives; octreotide; cisapride; anticholinergics; opioids; calcium channel blockers, DNA for delivery to the cells of the colon, glucosamine, thromboxane $A_2$ synthetase inhibitor such as Ridogrel, 5HT3-antagonist such as ondansetron, antibodies against infectioneous bacteriae such as clostiduim defficle.

The composition can also be used for delivery of an antiviral agent for example the prophylaxis of HIV.

Alternatively, the drug may be one which is systemically active and for which absorption may be improved in the colon region. Such drugs include polar compounds such as: heparins; insulin; calcitonins; human growth hormone (hGH) growth hormone releasing hormone (GHRH); interferons; somatostatin and analogues such as octreotide and vapreotide; erythropoietin (EPO); granulocyte colony stimulating factor (G-CSF); parathyroid hormone (PTH); luteinising hormone releasing hormone (LHRH) and analogues; atrial natriuretic factor (ANF); vasopressin, desmopressin, calcitonin gene related peptide (CGRP) and analgesics such as morphine.

The composition can also be used for delivery of DNA either as a vaccine or for therapeutic purposes where a drug is expressed for local or systemic effect.

The drug delivery composition of the invention may also be used for once-daily administration of drugs such as: captopril; alfuzosine; bisphosphonates such as clodronate;

carbamazepine; atenolol; benazepril. The colon may also be a useful place to delivery drugs to alter their metabolism, such as raloxifene and benazepril.

The starch capsules of the present invention are cheap and easy to manufacture fill and coat. They have been found to provide colon-specific delivery in a reliable manner. The starch capsules have been found to give good adhesion of the coating and their high density enables a good tumbling action. Aqueous coating is possible and the capsule walls have high mechanical strength and are non-flexible. Unlike gelatin capsules, the starch capsules are not brittle and this is particularly advantageous.

A further additional advantage of the use of a starch capsule is that the starch when released in the colonic environment will provide enhanced stabilisation of a peptide or protein drug.

It is known (Smith et al., Gastroenterology, 108 (suppl), 1995, A753) that the delivery of starch into the colon at a quantity of 10 mg/ml can lead to the reduced degradation of polypeptides. For the present invention the capsule comprises about 400 mg of starch. This will be delivered into a volume of about 50 ml leading to a starch concentration effective for polypeptide stabilisation.

Preferred embodiments of the invention will now be described in the following examples and with reference to the accompanying drawings in which.

EXAMPLES

Example 1

Figure 1:
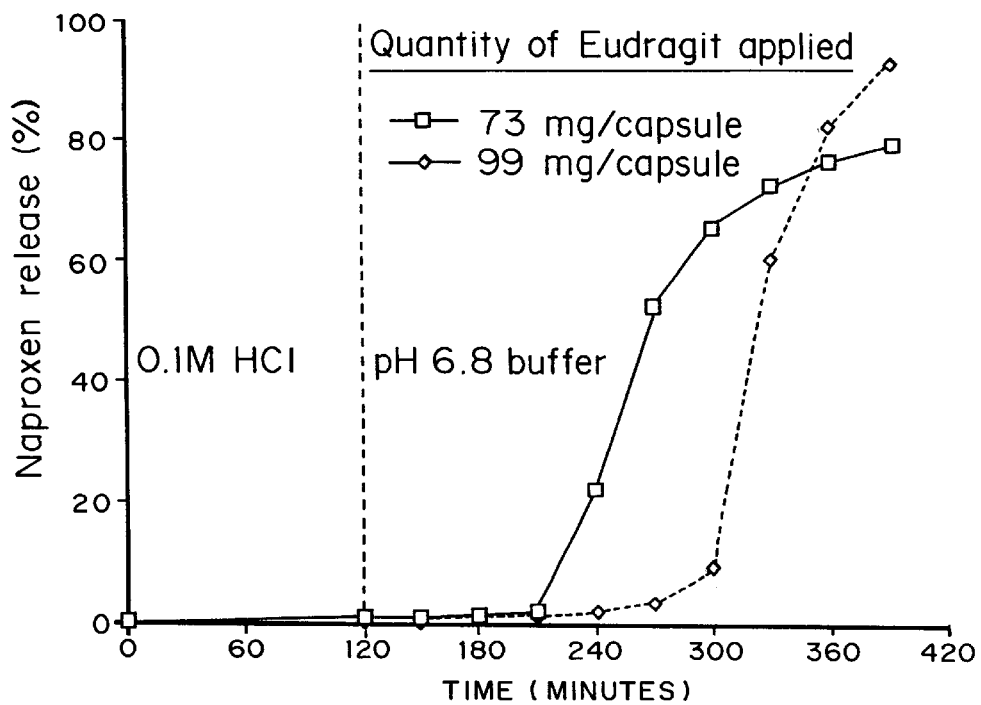
FIG. 1 shows the release profile of naproxen from various Eudragit coated starch capsules.

Starch capsules were filled with a blend comprising (by weight) 20% naproxen sodium, 75% spray-dried lactose and 5% Ac-Di-Sol. The mean capsule fill weight was 390 mg. Capsules were coated with a solution comprising 20 g of hydroxypropyl methylcellulose (Methocel E5M), 2 g of triacetin and 200 ml of water. Coating was performed using an Aeromatic STREA-1 fluid bed coater with bottom spray gun. The mean amount of HPMC applied to each capsule was 25 mg.

39 g of Eudragit L100 and 13 g of Eudragit S100 were dissolved in a mixture of 650 ml of and 20 ml of water. 10 g of dibutyl phthalate was mixed into the Eudragit solution. Finally, 10 g of talc was carefully mixed into a paste using 100 ml of isopropanol. The isopropanol/talc dispersion was added to the solution containing the Eudragits and plasticiser. The coating solution was applied to the HPMC-coated starch capsules using the Aeromatic STREA-1 fluid bed coater. The capsules were coated to a mean weight gain of 73 mg and 99 mg of Eudragit coating per capsule.

The dissolution performance of the capsules coated with HPMC/Eudragit was tested using the USP Method I (baskets rotating at 50 rpm). For the first 2 h of the test, 0.1M HCl was used as the test medium. After 2 h, the test medium was changed to 0.05M phosphate buffer, pH 6.8. Samples were withdrawn at regular intervals from the dissolution vessels and the appearance of naproxen sodium was monitored spectrophotometrically.

Results from the dissolution test are presented in FIG. 1. Capsules having 73 mg of Eudragit coating resisted drug release for a period of 2 h in acid followed by 90 minutes in pH 6.8 buffer. Capsules having 99 mg of Eudragit coating resisted drug release for a period of 2 h in acid followed by 120 mins in pH 6.8 buffer.

Example 2

Starch capsules were filled with a blend comprising (by weight) 20% naproxen sodium, 75% spray-dried lactose and 5% Ac-Di-Sol. The mean capsule fill weight was 390 mg. Capsules were coated with a solution comprising 20 g of hydroxypropyl methylcellulose (Methocel E5M), 2 g of triacetin and 200 ml of water. Coating was performed using an Aeromatic STREA-1 fluid bed coater with bottom spray gun. The mean amount of HPMC applied to each capsule was 25 mg.

The enteric coating was based on cellulose acetate phthalate (CAP, Eastman Chemicals, Kingsport, Tenn.). 70 g of CAP was dissolved in a mixture of 350 ml of acetone and 350 ml of ethanol. 17.5 g of diethyl phthalate (plasticiser) was mixed into the CAP solution. The coating solution was applied to the HPMC-coated starch capsules using the Aeromatic STREA-1 fluid bed coater.

The dissolution performance of the capsules coated with HPMC/CAP was tested using the USP Method I (Baskets rotating at 50 rpm). For the first 2 h of the test, 0.1M HCl was used as the test medium. After 2 h, the test medium was changed to 0.05M phosphate buffer, pH 6.8. Samples were withdrawn at regular intervals from the dissolution vessels and the appearance of naproxen sodium was monitored spectrophotometrically.

Capsules having 110 mg of CAP coating resisted drug release for a period of 2 h in acid followed by 2 h in pH 6.8 buffer. Thereafter, the capsules began to release naproxen sodium.

Example 3

Starch capsules were filled with a blend comprising (by weight) 94.2% spray-dried lactose, 3.33% samarium oxide and 2.5% Ac-Di-Sol. The mean capsule fill weight was 430 mg. Capsules were coated with a solution comprising 20 g of hydroxypropyl methylcellulose (Methocel E5M), 2 g of PEG 400 and 200 ml of water. Coating was performed using an Aeromatic STREA-1 fluid bed coater with bottom spray gun. The mean amount of HPMC applied to each capsule was 31 mg.

39 g of Eudragit L100 and 13 g of Eudragit S100 were dissolved in a mixture of 650 ml of isopropanol and 20 ml of water. 10 g of dibutyl phthalate was mixed into the Eudragit solution. Finally, 10 g of talc was carefully mixed into a paste using 100 ml of isopropanol. The isopropanol/talc dispersion was added to the solution containing the Eudragits and plasticiser. The coating solution was applied using the Aeromatic STREA-1 fluid bed coater. The capsules coated with HPMC were coated with the Eudragit solution to a mean weight gain of 89 mg per capsule.

The dissolution performance of the capsules coated with HPMC/Eudragit was tested using the USP Method I (baskets rotating at 50 rpm). For the first 2 h of the test, 0.1M HCl was used as the test medium. After 2 h, the test medium was changed to 0.05M phosphate buffer, pH 6.8. The dissolution vessels were visually inspected at regular intervals for the appearance of starch residue, which would indicate failure of the coating. The capsules remained intact after the 2 h incubation in acid. Coat failure commenced after a period of 2 h 40 mins in pH 6.8 buffer.

The in vivo performance of these capsules was assessed in a group of 9 healthy human subjects (5 male, 4 female, mean age 66 yrs.). Capsules were neutron-irradiated to generate the gamma isotope, $^{153}$samarium oxide. One of the radiolabelled capsules was administered to each of the 9 subjects. The passage of the capsules through the gastrointestinal tract was monitored externally using a gamma camera. The time of disintegration and the point in the GI tract where disintegration commenced was determined.

All capsules were found to disintegrate in the colon region. One capsule disintegrated at the ileo-caecal junction, two disintegrated in the ascending colon, two disintegrated at the hepatic flexure, two disintegrated in the transverse colon, one disintegrated at the splenic flexure and one disintegrated in the descending colon. The mean disintegration time after the capsules had left the stomach was 6.0 hours (see Table 1).

TABLE 1

In vivo performance of enteric-coated starch capsules

| Subject | Position of disintegration | Disintegration time (hours) | |
|---|---|---|---|
| | | Post dose | Post gastric emptying |
| 1 | Ascending colon | 4.7 | 4.2 |
| 2 | Splenic flexure | 6.4 | 5.9 |
| 3 | Descending colon | 8.8 | 8.3 |
| 4 | Transverse colon | 7.0 | 6.5 |
| 5 | Hepatic flexure | 6.7 | 6.2 |
| 6 | Ileo-caecal junction | 5.3 | 5.0 |
| 7 | Transverse colon | 8.7 | 8.3 |
| 8 | Hepatic flexure | 5.0 | 2.5 |
| 9 | Ascending/transverse colon | 7.3 | 6.8 |
| | | Mean | 6.0 |
| | | Std. dev. | 1.9 |

Example 4

Hard gelatin capsules were filled with a blend comprising (by weight) 96% microcrystalline cellulose and 4% samarium oxide. The mean capsule fill weight was 240 mg. The capsule lid and body were sealed together by the application of a thin layer of gelatin solution to the join. Capsules were coated with hydroxypropyl methylcellulose and then with the mixed Eudragit formulation, as described in Example 3. The mean weight of Eudragit coating applied to each capsule was 58 mg.

The dissolution performance of the coated capsules was tested under the conditions detailed in Example 3. The capsules remained intact after the 2 h incubation in acid. Coat failure commenced after a period of 70 mins in pH 6.8 buffer.

The capsules were neutron-irradiated and administered to the same group of nine individuals as in Example 3 as part of a cross-over study. Seven out of nine capsules disintegrated in the colon. The two remaining capsules disintegrated in the small intestine. The mean disintegration time after the capsules had left the stomach was 3.0 hours (see Table 2).

Compared to the starch gelatin capsules given in Example 3, the time to disintegration of the gelatin capsules was shorter, which reflected the smaller amount of Eudragit coating applied. However, the variability in disintegration time post-gastric emptying was greater for the gelatin capsules (coefficient of variation=46.7%) compared to the starch capsules (coefficient of variation 31.7%).

TABLE 2

In vivo performance of enteric-coated hard gelatin capsules

| Subject | Position of disintegration | Disintegration time (hours) | |
|---|---|---|---|
| | | Post dose | Post gastric emptying |
| 1 | Ascending/transverse colon | 5.4 | 4.3 |
| 2 | Descending colon | 5.0 | 4.4 |
| 3 | Ascending colon | 4.3 | 3.8 |
| 4 | Ascending colon | 6.0 | 3.5 |
| 5 | Descending colon | 10.5 | 4.2 |
| 6 | Ascending colon | 3.3 | 2.8 |
| 7 | Small intestine | 1.0 | 0.5 |
| 8 | Hepatic flexure | 4.3 | 1.3 |
| 9 | Small intestine | 3.0 | 2.5 |
| | | Mean | 3.0 |
| | | Std. dev | 1.4 |

Example 5

Figure 2:
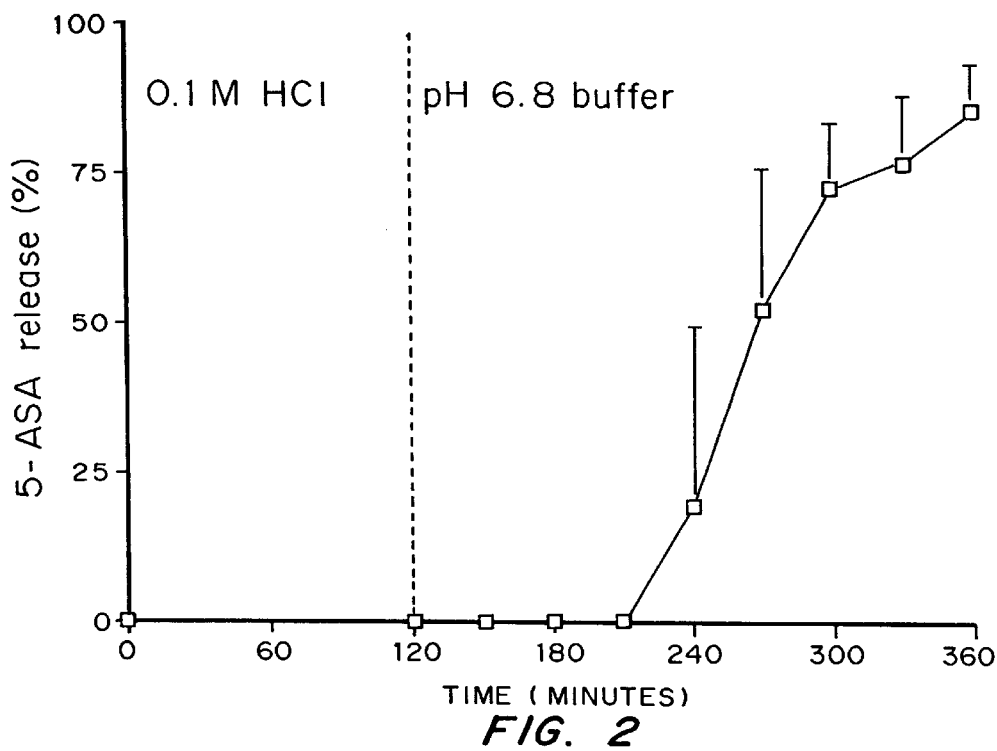
FIG. 2 shows the dissolution performance of coated starch capsules containing 5-ASA.

Starch capsules were prepared each containing 300 mg of 5-amino salicylic acid (5-ASA), 100 mg of lactose, and 20 mg of samarium oxide. 5-ASA is well absorbed from the upper intestine resulting in undesirable side effects but poorly absorbed from the colon here is has topical antiinflammatory activity. Thus colon targeted dosage forms are the formulation of choice for this drug. Some of the capsules were coated, using an Aeromatic STREA-1, with 40 mg of HPMC subcoat and 93 mg of the Eudragit L/S coating of the composition described in Example 3. The dissolution performance of the coated capsules is shown in FIG. 2. The capsules resisted drug release for 2 h in acid followed by 90 minutes in pH 6.8 buffer.

Figure 3:
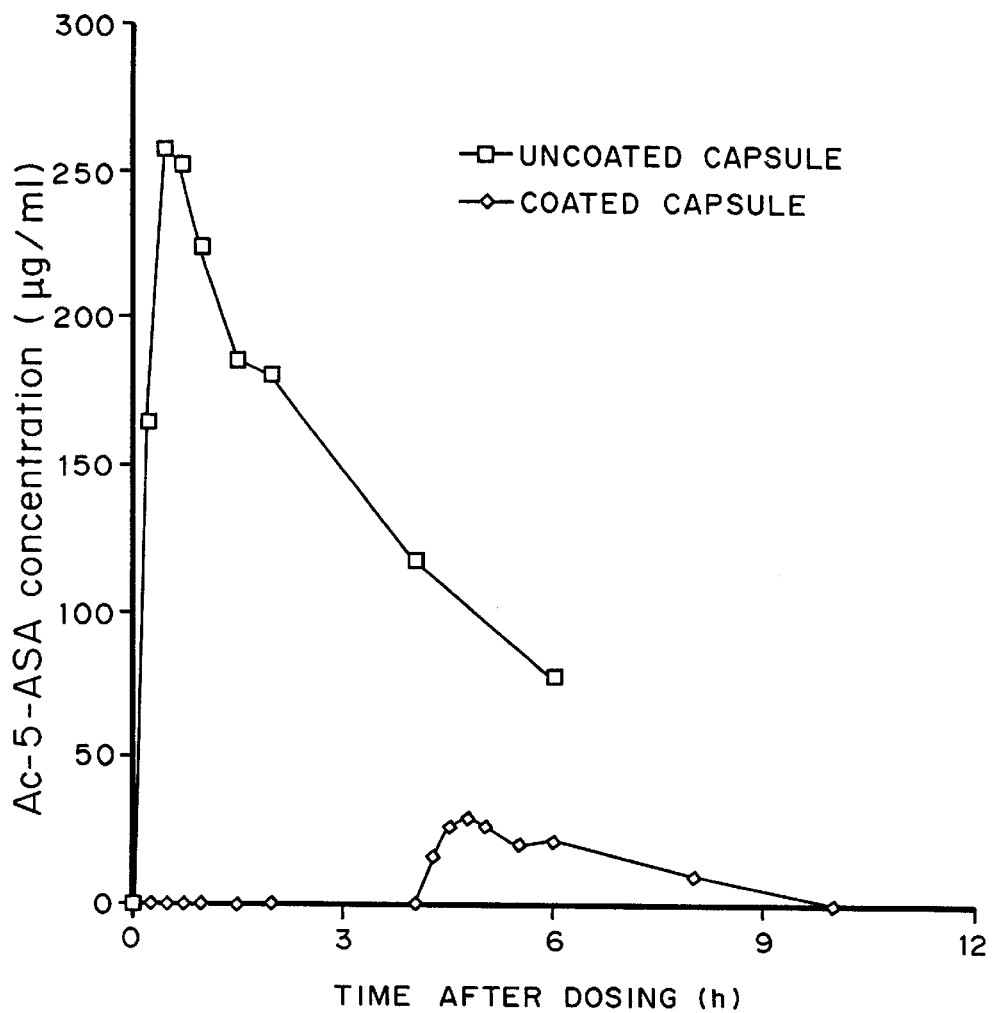
FIG. 3 shows the plasma concentration of acetyl-5-ASA following administration of 5-ASA in uncoated and coated starch capsule formulations.

The in vivo performance of the coated and uncoated capsules was assessed in a two-way cross-over study in a group of 8 volunteers (5 male, 3 female, mean age 64 years). Capsules were neutron-irradiated to generate the gamma isotope $^{153}$samarium oxide. On each occasion, one of the radiolabelled capsules was administered to each of the 8 subjects. The passage of the capsules through the gastrointestinal tract was monitored externally using a gamma camera. Plasma samples were collected at frequent intervals and assayed for acetyl-5-ASA content. All of the uncoated capsules disintegrated in the stomach and small intestine within 30-minutes of dosing. In 2 of the 8 subjects disintegration of the coated capsules commenced in the lower small intestine. In the remaining subjects, distegration commenced in the ileocaecal junction or ascending colon. Mean concentration vs. time profiles for the two formulations are shown in FIG. 3. With the uncoated formulation there was rapid absorption of 5-ASA. With the coated formulation, no drug was detected in plasma until 4–6 hours after dosing. The peak plasma level was very much lower with coated formulation indicating selective delivery of 5-ASA into the distal intestines.

Example 6

Starch and hard gelatin capsules were filled with a powder blend comprising 6% w/w paracetamol and 94% w/w microcrystalline cellulose. Paracetamol was used as a model drug. The starch and hard gelatin capsules were subcoated with a layer of HPMC and overcoated with the Eudragit L/S mixture (as described in Example 3). The dissolution performance of six starch capsules and six gelatin capsules was measured using the test procedure described in Example 3, with dissolution medium being assayed for paracetamol content using UV spectrophotometry. The capsules were blister-packed using a PVC/PVdC laminate and stored at a temperature of 40° C. and relative humidity of 75% for a period of 6 months. After 6 months, the dissolution performance of the capsules was retested. The mean time for 50% paracetamol release from the capsules was calculated from the dissolution data. The results are recorded in Table 3.

| | Time for 50% drug release (mean + SD, n = 6 | |
|---|---|---|
| Formulation | At start | After 6 months at 40% C/ 75% RH |
| Blister-packed gelatin | 203 ± 5 min | 292 ± 13 min |
| Blister-packed starch | 317 ± 30 min | 351 ± 35 min |

For the gelatin capsules, there was a large (44%) and statistically signficant increase (p<0.05, Student's t-test) in the time for 50% drug release. Although there was an increase in the time for 50% release for the starch capsules, it was smaller in magnitude (11%) and was not statistically significant. The results from this accelerated stability study indicated a significant change in dissolution performance for the coated hard gelatin capsules. Coated starch capsules stored under the same conditions did not show any change in dissolution performance. It was noted that the coated hard gelatin capsules had become more brittle after storage and the coating detached extremely easily from the capsule shell. Such physical changes were not apparent for the coated starch capsules.

What is claimed is:

1. A drug delivery composition for delivering a drug to the colonic region comprising a starch capsule containing the drug,
    wherein the starch capsule is provided with a coating comprising a poly(methylmethacrylate) or a copolymer of methacrylic acid and methyl methacrylic which dissolves at a pH of 5 or higher, and
    wherein the coating has a thickness between 80 μm and 200 μm and dissolves to expose the capsule about 3 to 4 hours after oral administration of the composition such that the capsule will not release the drug until the capsule is in the colon and/or terminal ileum.

2. The drug delivery composition of claim 1 wherein the drug is one which acts locally in the colon.

3. The drug delivery composition of claim 1 wherein the drug is for systemic delivery and systemic action.

4. The drug delivery composition of claim 1 wherein the drug is a vaccine for delivery to the lymphoid tissue of the colon.

5. A method of delivering a drug to the colonic region of a human or mammal comprising:
    orally administering a drug delivery composition comprising a starch capsule containing the drug, wherein the starch capsule is provided with a coating comprising a poly(methacrylate) or a copolymer of methacrylic acid and methyl methacrylate which dissolves at a pH of 5 or higher, and wherein the coating has a thickness between 80 μm and 200 μm and dissolves to expose the capsule about 3 to 4 hours after oral administration of the composition such that the capsule will not release the drug until the capsule is in the colon and/or terminal ileum.

6. A method of delivering a vaccine to the lymphoid tissue present in the colon of a human or mammal comprising:
    orally administering a drug delivery composition comprising a starch capsule containing the drug, wherein the starch capsule is provided with a coating comprising a poly(methacrylate) or a copolymer of methacrylic acid and methyl methacrylate which dissolves at a pH of 5 or higher, and wherein the coating has a thickness between 80 μm and 200 μm and dissolves to expose the capsule about 3 to 4 hours after oral administration of the composition such that the capsule will not release the vaccine until the capsule is in the colon and/or terminal ileum.

7. The composition of claim 1 wherein the coating dissolves at a pH of between 6 and 7.

8. The drug delivery composition of claim 1 wherein the coating comprises a copolymer of methacrylic acid and methylmethacrylate.

9. The drug delivery composition of claim 8 wherein the copolymer is a combination of EUDRAGIT L100 and EUDRAGIT S100.

10. The drug delivery composition of claim 9 wherein the ratio EUDRAGIT L100:EUDRAGIT S100 is between 100:0 and 20:80.

11. The drug delivery composition of claim 10 wherein the ratio EUDRAGIT L100:EUDRAGIT S100 is between 70:30 and 80:20.

12. The drug delivery composition of claim 10 wherein the coating thickness is between about 80 and 120 μm.

13. The drug delivery composition of claim 11 wherein the coating thickness is between about 150 and 200 μm.

* * * * *